United States Patent [19]
Fan et al.

[11] Patent Number: 5,731,087
[45] Date of Patent: Mar. 24, 1998

[54] LUBRICIOUS COATINGS CONTAINING POLYMERS WITH VINYL AND CARBOXYLIC ACID MOIETIES

[75] Inventors: You Ling Fan, East Brunswick; Lawrence Marlin, Bridgewater; Lisa M. Bouldin, Cranford; Isabel Maria Marino, Somerset, all of N.J.

[73] Assignee: Union Carbide Chemicals & Plastics Technology Corporation, Danbury, Conn.

[21] Appl. No.: 478,990

[22] Filed: Jun. 7, 1995

[51] Int. Cl.$^6$ .............................. A61L 29/00; A61L 31/00; C08J 7/04

[52] U.S. Cl. .............. 428/412; 428/424.2; 428/424.4; 428/424.6; 428/424.8; 428/425.1; 428/425.5; 428/441; 428/447; 428/448; 428/451; 428/461; 428/462; 428/463; 428/475.8; 428/483; 428/510; 428/515; 428/518; 428/520; 428/522; 604/266

[58] Field of Search ............... 428/412, 424.6, 428/475.8, 483, 441; 604/266; 424/424.2, 424.4, 424.8, 425.1, 425.5, 447, 448, 451, 461, 462, 463, 510, 515, 518, 520, 522

[56] References Cited

U.S. PATENT DOCUMENTS

| | | | |
|---|---|---|---|
| 3,264,202 | 8/1966 | King | 204/159.14 |
| 3,387,061 | 6/1968 | Smith et al. | 260/874 |
| 3,642,943 | 2/1972 | Noel | 260/859 R |
| 3,663,288 | 5/1972 | Miller | 117/7 |
| 3,756,238 | 9/1973 | Hanke | 128/270 |
| 3,898,143 | 8/1975 | Assarsson et al. | 204/159.12 |
| 3,900,378 | 8/1975 | Yen et al. | 204/159.14 |
| 3,992,552 | 11/1976 | Assarsson et al. | 204/159.12 |
| 3,993,551 | 11/1976 | Assarsson et al. | 204/159.14 |
| 3,993,553 | 11/1976 | Assarsson et al. | 204/159.12 |
| 4,055,682 | 10/1977 | Merrill | 427/2 |
| 4,058,124 | 11/1977 | Yen et al. | 128/284 |
| 4,100,309 | 7/1978 | Micklus et al. | 427/2 |
| 4,119,094 | 10/1978 | Micklus et al. | 128/132 R |
| 4,169,163 | 9/1979 | Judd et al. | 426/413 |
| 4,232,608 | 11/1980 | Wrightson | 102/103 |
| 4,265,927 | 5/1981 | Ericksson et al. | 427/2 |
| 4,327,009 | 4/1982 | Allen et al. | 524/114 |
| 4,373,009 | 2/1983 | Winn | 428/424.2 |
| 4,442,145 | 4/1984 | Probst et al. | 427/385.5 |
| 4,459,317 | 7/1984 | Lambert | 427/2 |
| 4,479,795 | 10/1984 | Mustacich et al. | 604/53 |
| 4,487,808 | 12/1984 | Lambert | 428/423.1 |
| 4,499,124 | 2/1985 | Pusineri et al. | 427/385.5 |
| 4,526,579 | 7/1985 | Ainpour | 604/265 |
| 4,585,666 | 4/1986 | Lambert | 427/2 |
| 4,589,873 | 5/1986 | Schwartz et al. | 604/265 |
| 4,600,404 | 7/1986 | Sheldon et al. | 604/387 |
| 4,642,242 | 2/1987 | Solomon et al. | 427/2 |
| 4,642,267 | 2/1987 | Creasy et al. | 428/413 |
| 4,666,437 | 5/1987 | Lambert | 604/265 |
| 4,684,558 | 8/1987 | Keusch et al. | 428/40 |
| 4,707,381 | 11/1987 | Toyama et al. | 427/407.1 |
| 4,729,914 | 3/1988 | Kliment et al. | 428/36 |
| 4,769,013 | 9/1988 | Lorenz et al. | 604/265 |
| 4,773,901 | 9/1988 | Norton | 604/265 |
| 4,835,003 | 5/1989 | Becker et al. | 427/2 |
| 4,840,851 | 6/1989 | Gölander | 428/523 |
| 4,876,126 | 10/1989 | Takemura et al. | 428/35.7 |
| 4,906,237 | 3/1990 | Johansson et al. | 604/265 |
| 4,943,460 | 7/1990 | Markle et al. | 428/36.9 |
| 4,965,112 | 10/1990 | Brinkman et al. | 428/36.91 |
| 4,980,231 | 12/1990 | Baker et al. | 428/36.9 |
| 4,987,181 | 1/1991 | Bichon et al. | 525/54.1 |
| 4,990,357 | 2/1991 | Karakelle et al. | 427/2 |
| 5,001,009 | 3/1991 | Whitbourne | 428/412 |
| 5,037,677 | 8/1991 | Halpern et al. | 427/338 |
| 5,041,100 | 8/1991 | Rowland et al. | 604/265 |
| 5,077,352 | 12/1991 | Elton | 525/409 |
| 5,079,093 | 1/1992 | Akashi et al. | 428/411.1 |
| 5,084,315 | 1/1992 | Karimi et al. | 428/36.6 |
| 5,091,205 | 2/1992 | Fan | 427/2 |
| 5,135,516 | 8/1992 | Sahatjian et al. | 604/265 |
| 5,229,211 | 7/1993 | Murayama et al. | 428/424.4 |
| 5,270,086 | 12/1993 | Hamlin | 428/35.2 |
| 5,295,978 | 3/1994 | Fan et al. | 604/265 |
| 5,304,121 | 4/1994 | Sahatjian | 604/53 |
| 5,331,027 | 7/1994 | Whitbourne | 524/37 |

FOREIGN PATENT DOCUMENTS

| | | |
|---|---|---|
| 0028122 | 5/1981 | European Pat. Off. |
| 0106004 | 4/1984 | European Pat. Off. |
| C166998 | 1/1986 | European Pat. Off. |
| 0480809A3 | 4/1992 | European Pat. Off. |
| 0586324A1 | 3/1994 | European Pat. Off. |
| 8928923 | 2/1988 | Japan. |
| WO8907521 | 8/1989 | WIPO. |
| 8909246 | 10/1989 | WIPO. |

*Primary Examiner*—Frederick Krass
*Attorney, Agent, or Firm*—W. K. Volles

[57] ABSTRACT

Lubricious coatings comprising a binder polymer having a vinyl moiety and a carboxylic acid moiety and a hydrophilic polymer are disclosed. The coatings can be applied to a variety of substrates such as, for example, catheters, stents, dilatation balloons, guide wires, endotracheal tubes, instruments, implants and other biomedical devices and can provide exceptional lubricity and abrasion resistance. Processes for applying the lubricious coatings in either one or two coating steps are also disclosed.

17 Claims, No Drawings

LUBRICIOUS COATINGS CONTAINING POLYMERS WITH VINYL AND CARBOXYLIC ACID MOIETIES

FIELD OF THE INVENTION

This invention relates to lubricious coatings for substrates such as, for example, biomedical devices. More specifically, the present invention relates to lubricious coatings containing a hydrophilic polymer which is lubricious in an aqueous environment and a binder polymer to adhere the hydrophilic polymer to the substrate.

BACKGROUND OF THE INVENTION

A variety of lubricious coatings have been proposed for use on biomedical devices such as, for example, catheters, guide wires, endotracheal tubes and implants. Common materials used in the art to provide lubricious coatings for biomedical devices include, for example, oil, silicone and polymeric materials, such as polyN-vinylpyrrolidone, hydrophilic polyurethanes, Teflon, polyethylene oxide and polyacrylic acid. Among the most common materials used to provide lubricious coatings are hydrophilic polymers which are covalently bonded to the substrate with a binder polymer having reactive functional groups, e.g., isocyanate, aldehyde and epoxy groups. Although the use of such binder polymers having reactive functional groups is effective to provide lubricious coatings having a high degree of abrasion resistance, such binder polymers are often highly reactive, toxic and typically require special handling techniques in order to avoid potential health, safety and environmental problems.

Accordingly, new improved lubricious coatings are desired which utilize binder polymers which are less toxic than those which contain highly reactive functional groups, such as isocyanates, yet which can provide a high degree of lubricity and abrasion resistance.

SUMMARY OF THE INVENTION

In accordance with the present invention, improved lubricious coatings are provided for use on biomedical devices such as, for example, catheters, guide wires, endotrachael tubes, balloons and implants. The coatings have a hydrophilic polymer which is substantially more lubricious when wetted with an aqueous liquid than when dry, and a binder polymer which is capable of bonding to the surface of the biomedical device and the hydrophilic polymer. The binder polymers suitable for use in accordance with the present invention are copolymers which comprise a vinyl moiety, preferably vinyl chloride or vinyl acetate, and a carboxylic acid moiety.

By the present invention, it is now possible to provide lubricious coatings for substrates which can provide exceptional lubricity and abrasion resistance without the need for using highly reactive, toxic chemicals to covalently bond the hydrophilic polymer to the surface of the substrate.

DETAILED DESCRIPTION OF THE INVENTION

The binder polymers suitable for use in accordance with the present invention are copolymers, i.e., polymers made from two or more monomers, which comprise at least one vinyl moiety and at least one carboxylic acid moiety. The vinyl moiety and the carboxylic acid moiety can be present in the same monomer or in different monomers.

The vinyl moiety can be derived from any monomer having a vinyl group such as, for example, commonly found in compounds such as vinyl chloride, vinyl acetate and similar esters. Preferably, the vinyl moiety has the formula ($CH_2$=CH—). Typically, the monomers which contain the vinyl moiety comprise from about 2 to 20 carbon atoms per molecule, more often from about 2 to 8 carbon atoms per molecule. Such vinyl monomers may contain one or more, e.g., 2 or 3, vinyl groups per molecule. Preferably, the vinyl monomer is water-insoluble. Without being bound to any particular theory, it is believed that polymeric moieties derived from water-insoluble vinyl monomers can provide enhanced adhesion of the binder polymers to substrates as compared to water-soluble vinyl monomers. As used herein, the term "water-soluble" means that at least a 10 weight percent ("wt. %") solution of the monomer is soluble in water.

Examples of vinyl monomers which may be suitable for use in accordance with the present invention include, without limitation, vinyl halides, e.g., vinyl chloride, vinyl fluoride, vinyl bromide, vinyl trichloride; vinyl ethers, e.g., vinyl ethyl ether, vinyl butyl ether, vinyl ethylhexyl ether; vinyl esters, e.g., vinyl acetate, vinyl butarate, vinyl stearate, vinyl propionate, vinyl ethylhexonate; vinyl methyl ketone, vinyl acetylene, butadiene, vinyl alcohol (produced in situ through hydrolysis of vinyl acetate moieties in the polymer) and vinylidene compounds. Vinyl halides, including vinyl chloride, vinyl fluoride and vinyl bromide, are preferred vinyl monomers for use in accordance with the present invention. Vinyl chloride is an especially preferred monomer for use in accordance with the present invention. Vinyl ester monomers, and in particular vinyl acetate, are also preferred for use in accordance with the present invention. Combinations of vinyl halides and vinyl esters, e.g., vinyl chloride and vinyl acetate, are especially preferred.

The total concentration of vinyl monomers in the binder polymer is typically from about 10 to 99.9 mole %, preferably from about 50 to 99.5 mole %, and, more preferably, from about 70 to 99 mole %. The selection of particular vinyl monomers and their proportions in the binder polymer should be selected in order to provide enhanced bonding to the surface of the substrate to be coated. For instance, a vinyl monomer that is identical or substantially similar, or compatible to one or more monomeric repeating units present in the substrate is preferred to provide enhanced physical bonding between the polymer binder and the substrate. More than one vinyl monomer may be used. Further details concerning the selection and amounts of the vinyl monomers are known to those skilled in the art. In addition, such vinyl monomers are commercially available.

The carboxylic acid moiety can be derived from any organic acid containing a carboxyl group. Typically, the carboxylic acids contain from 1 to about 26, more typically, from 1 to 8 carbon atoms per molecule. Preferred carboxylic acids include, but are not limited to, acrylic, methacrylic, maleic, itaconic, fumaric, and the like. Other carboxylic acids such as, for example, unsaturated fatty acids, and polymerizable aromatic and alicyclic carboxylic acids may also be employed. In addition to the above-mentioned carboxylic acids, the corresponding anhydrides, e.g., maleic anhydride, may also be used, provided that the anhydride is hydrolyzed to its acid form in order to promote bonding of the hydrophilic polymer. Otherwise, inferior abrasion resistance may result. The carboxylic acid groups may be present in their free acid form or partially neutralized, provided that there is a sufficient amount of free acid to promote bonding between the hydrophilic polymer and the binder polymer.

The total concentration of the carboxylic-containing monomer in the binder polymer typically ranges from about 0.1 to 20 mole % and, preferably, from about 0.5 to 5 mole %. The mount of carboxylic acid monomer should be selected in order to provide enhanced bonding of the hydrophilic polymer to the binder polymer and substrate. Further details concerning the selection and amounts of the carboxylic acid-containing monomers are known to those skilled in the art. In addition, such carboxylic acid monomers are commercially available.

In addition to the vinyl and carboxyl-containing monomers defined above, one or more other monomers can be used as additional monomers in the binder polymers of the present invention. Such additional monomers may be introduced, for example, in order to provide desired physical, mechanical or chemical properties to the binder polymer, e.g., solubility, processability, melting temperature, glass transition temperature, hardness, tensile strength and the like. Examples of these monomers include isoprene, hydroxyethyl acrylate, alpha-methyl styrene, propylene, ethyl acrylate, methyl methacrylate, sulfonated acrylates, and the like.

Preferably, the selection and amounts of monomers used to prepare the binder polymers of the present invention are effective to provide a binder polymer having the desired degree of adhesion and flexibility when applied to the substrate. Certain binder polymers may be more effective on certain substrates than on others. Further details concerning the selection and amounts of the monomers used to make the binder polymers are known to those skilled in the art. In addition, it is preferred that the binder polymers of the present invention have a molecular weight of from about 5,000 to 1,000,000, more preferably from about 20,000 to 500,000 and most preferably from about 20,000 to 100,000 grams per gram mole. As used herein, the term "molecular weight" means member average molecular weight. Techniques for determining the number average molecular weight are known to those skilled in the art.

Typical copolymers suitable for use as binder polymers in accordance with the present invention include, but are not limited to, maleic acid-vinyl chloride-vinyl acetate, acrylic acid-vinyl chloride-vinyl acetate, maleic acid-vinyl chloride-vinyl acetate-vinyl alcohol, acrylic acid-styrene-vinyl acetate, maleic acid-vinyl ether, and acrylic acid-styrene-butadiene polymers. These polymers may be polymerized in a random, block or grafted polymer form. Further details concerning the preparation of such copolymers are known to those skilled in the art. In addition, many of the copolymers described above are commercially available from a variety of sources.

The hydrophilic polymers suitable for use in accordance with the present invention are any water-soluble or water-swellable polymers which are substantially more lubricious when wetted with an aqueous liquid than when dry. As used herein, the term "water-swellable" means a substantially hydrophilic polymer which, even though is not soluble in water, would absorb sufficient water to render it lubricious in the hydrated state. In addition, the term "hydrophilic" as used herein means that water droplets do not readily form beads on the surface of such hydrophilic material, but instead, the water droplets tend to assume a contact angle of less than 45° and readily spread on its surface.

Preferred hydrophilic polymers include, but are not limited to, those selected from the group consisting of polyvinyl compounds, polysaccharides, polyurethanes, polyacrylates, polyacrylamides, polyalkylene oxides, and copolymers, complexes, mixtures, and derivatives thereof. PolyN-vinyl lactams are preferred polyvinyl compounds for use in accordance with the present invention. The term "polyN-vinyl lactam" as used herein means homopolymers and copolymers of such N-vinyl lactams as N-vinylpyrrolidone, N-vinylbutyrolactam, N-vinylcaprolactam, and the like, as well as the foregoing prepared with minor amounts, for example, up to about 20 weight percent, of one or a mixture of other vinyl monomers copolymerizable with the N-vinyl lactams. Of the polyN-vinyl lactams, the polyN-vinylpyrrolidone homopolymers are preferred. A variety of polyN-vinylpyrrolidones are commercially available and of these a polyN-vinylpyrrolidone having a K-value of at least about 30 is especially preferred. The K valve is a measure of molecular weight, the details of which are known to those skilled in the art. Other preferred hydrophilic polymers for use in accordance with the present invention include, but are not limited to, those selected from the group consisting of N-vinylpyrrolidone-hydroxyethyl acrylate copolymers, carboxymethylcellulose, hydroxyethyl cellulose, polyacrylamide, polyhydroxyethyl-acrylate, cationically-modified hydroxyethylcellulose, polyacrylic acid, polyethylene oxides, and complexes, mixtures, and derivatives thereof. Especially preferred are polyN-vinylpyrrolidone, polyethyleneoxide and cellulosics, such as, for example, carboxymethylcellulose and cationically modified cellulose.

The hydrophilic polymers suitable for use in accordance with the present invention can be nonionic, cationic, anionic or amphoteric. Typically, the molecular weight of the hydrophilic polymers is from about 100,000 to 10,000,000 grams per gram mole, preferably from about 200,000 to 5,000,000 grams per gram mole, and, more preferably, from about 300,000 to 2,000,000 grams per gram mole. Further details concerning the preparation and selection of hydrophilic polymers suitable for use in accordance with the present invention are known to those skilled in the art. Such hydrophilic polymers are readily commercially available from a variety of sources such as, for example, Union Carbide Corporation, Danbury, Conn.

It is preferred in accordance with the present invention that the hydrophilic polymer is bonded to the binder polymer by hydrogen or ionic bonds. While not necessary for practicing this invention, there may be some degree of covalent bonding between the binder polymer and the hydrophilic polymer. However, preferably, there is a substantial absence, i.e., less than about 5%, more preferably less than about 1%, of covalent bonds between the binder polymer and the hydrophilic polymer based on the total number of bonding sites between the binder polymer and the hydrophilic polymer. It is also preferred that there is a substantial absence, i.e., less than about 5%, more preferably less than about 1%, of highly reactive functional moieties selected from the group consisting of isocyanate, aldehyde and epoxy moieties in the binder polymer.

In addition to the binder polymers and the hydrophilic polymers, the lubricious coatings of the present invention may comprise one or more additives normally used in coating formulations such as, for example, surfactants, preservatives, viscosity modifiers, pigments, dyes, and other additives known to those skilled in the art. Additionally, other functional additives which are ionically bonded to the hydrophilic polymer may also be used. These additives include ingredients such as, for example, therapeutic agents, antithrombogenic agents, antimicrobial agents and antibiotic agents. When ionic additives are employed in the coating, e.g., heparin, which is anionic, it is preferred to use a cationic hydrophilic polymer, e.g., a cationically-modified hydroxyethylcellulose. Similarly, when an additive is cationic, it is preferred to use an anionic hydrophilic polymer, e.g., a polyacrylic acid-acrylamide polymer. When an antimicrobial agent such as 2,4,4'-trichloro-2'-chloroxydiphenyl ether is used as an additive, either an ionic or nonionic hydrophilic polymer may be employed. The combination of an additive and a hydrophilic polymer may be varied as needed to provide the desired performance.

The substrates to which the lubricious coatings of the present invention can be applied are not limited. The substances which are usable for the substrates include, but are not limited to, various organic polymeric compounds such as, for example, polyamides, polyesters, e.g., polyethylene terephthalate and polystyrene terephthalate, polyvinyl chloride, polyvinylidene chloride, polystyrene, polyacrylic esters, polymethylmethacrylate and other polymethacrylic esters, polyacrylonitrile, polyethylene, polypropylene, polyurethane, polyvinyl acetate, silicone resins, polycarbonate, polysulfone, polybutadiene-styrene copolymers, polyisoprene, nylon, polyethylene, polypropylene, polybutylene, halogenated polyolefins, various latexes, various copolymers, various derivatives and blends thereof, and various inorganic and metallic substances such as, for example, glass, ceramics, stainless steel, and a super elastic metal or shape memory alloys such as Ni—Ti alloy, for example. Typical substrates to which the lubricious coatings of the present invention can be applied include, but are not limited to, catheters, balloon catheters, guide wires, endotracheal tubes, implants and other biomedical devices such as, for example, the outer surface of an endoscope.

The lubricious coatings of the present invention may be applied by either a two-step coating process or a one-step coating process. In a two-step coating process, the portion of the substrate to be coated is first coated with the binder polymer and subsequently coated with the hydrophilic polymer. In a one-step coating process, the binder polymer and hydrophilic polymer are applied to the substrate in a single step. Any conventional liquid coating processes may be utilized in accordance with the present invention. Such processes include, for example, dip-coating, spray-coating, knife-coating and roller coating. Dip-coating is a preferred coating method in accordance with the present invention.

In the coating processes of the present invention, the binder polymers and the hydrophilic polymers may be delivered from liquids contained in either a solution, a dispersion or an emulsion of the polymers. In the one-step coating methods, the binder polymers and the hydrophilic polymers are contained in the same liquid medium. In the two-step methods, the binder polymers and the hydrophilic polymers are contained in separate liquid mediums. Additional coating steps may also be employed to introduce different polymers or additives. The liquid mediums used for delivering the binder polymers and hydrophilic polymers may be organic, aqueous or an organic-aqueous mixture. The liquid medium used for delivering the binder polymer can be selected so that it has some solvency for the substrate, i.e., when the substrate is polymeric. This can enhance the adhesion between the binder polymer and the substrate and aid to the film formation of the coating material. Preferred liquid mediums for delivering the binder polymers and hydrophilic polymers include, but are not limited to, esters, e.g., ethyl acetate, isopropyl acetate; alcohols, e.g., isopropyl alcohol, ethanol, butanol; ketones, e.g., acetone, methylethylketone, diacetone alcohol, methyl isobutyl ketone; amides such as dimethyl formamide; toluene; glycol ethers such as butyl glycol ether; chlorinated solvents such as dichloroethane, water, and mixtures thereof. Preferably, the liquid mediums are selected so that the binder polymers and hydrophilic polymer evenly wet the surface of the substrate to be coated.

Preferably, the concentration of the binder polymer and the hydrophilic polymers in the liquid mediums are sufficient to provide the desired amounts of the respective polymers in the lubricious coatings. Typically, the concentration of the binder polymers in the liquid medium will range from about 0.05 to 10 weight percent and, preferably, from about 0.2 to 2 weight percent based on the total weight of the liquid medium. Typically, the concentration of the hydrophilic polymers will range from about 0.1 to 20 weight percent and, preferably, from about 0.5 to 5 weight percent, based upon the total weight of the liquid medium. Further details concerning the selection of liquid mediums for delivering the binder polymers and hydrophilic polymers of the present invention are known to those skilled in the art.

The coating processes of the present invention are preferably conducted in a liquid phase at atmospheric pressure and at a temperature from about 20° to 90° C. The residence times for contacting the surface of the substrate to be coated with the liquid mediums containing the binder polymer or the hydrophilic polymer, or both, range from about 1 second to 30 minutes, preferably from about 10 seconds to 10 minutes. It is generally desirable to dry the coatings after application of the coating at a temperature from about 30° to 150° C., preferably in a forced-air oven. Microwave ovens and infrared heaters may also be used if desired. Typical drying times range from about 1 minute to 24 hours and preferably range from about 10 minutes to 5 hours. When a two-step coating process is employed, it is preferred to dry the binder polymer before application of the hydrophilic polymer.

The lubricious coatings which result from the coating processes of the present invention typically have a thickness of from about 0.05 to 10 microns, and preferably from about 0.1 to about 5 microns. When a two-step coating process is employed, the resulting coating preferably comprises an inner layer which is rich, i.e., greater than 50%, in the binder polymer which contacts the surface of the substrate, and an outer layer which is rich, i.e., greater than 50%, in the hydrophilic polymer which contacts the inner layer. The outer layer, which is rich in the hydrophilic polymer, has an outer surface which becomes lubricious when exposed to an aqueous liquid. When a one-step coating process is employed, the resulting coating comprises a single layer which is preferably a substantially homogeneous mixture of the binder polymer and the hydrophilic polymer. However, since the binder polymer will often have more affinity for the substrate than the hydrophilic polymer, it is believed that there may be a higher concentration of the binder polymer near the surface of the substrate.

The following examples are presented for illustrative purposes and are not intended to limit the scope of the claims which follow.

EXAMPLES

The following tests were employed in conducting the examples.

Contact Angle Test: The contact angle of distilled water on either coated or uncoated substrate was measured using a NRL Contact Angle Goniometer Model A-100(Rame'-hart, Inc., Mountain Lakes, N.J.) at room temperature. The average value of three measurements was used.

Coefficient of Friction Test: A pair of catheters is laid parallel to each other on a horizontal stainless steel platform at a distance of about 1.5 inches apart. The platform and the catheters are subsequently wetted thoroughly with about 100 milliliters ("ml") of distilled water. A rectangular shaped aluminum block (2×2×3 inches) weighing 100 grams ("g") wrapped in a wet cellulose acetate membrane is placed on top of the catheters at the free-moving end of the platform. Thereafter, the platform is raised gradually and steadily from the free-moving end until an inclination angle Ø is reached where the block begins to slide on the wet catheter surfaces. The coefficient of friction ("COF") is calculated as tangent Ø.

Abrasion Test—The abrasion resistance of the wet coating is measured by abrading the wet catheter through a silicone elastomer grommet (the inside diameter of the grommet is made to be about 10% smaller than the outside diameter of the catheter) for 100 abrasions, i.e., strokes. Each abrasion consists of a complete back and forth traveling of the catheter through the grommet. The COF of the abraded catheter is measured again and reported as the COF after abrasion.

The following ingredients were used in conducting the examples. All of the ingredients used in the Examples are commercially available from a variety of sources.

PVC—polyvinyl chloride
PVC endotracheal tubes—32 French size.
IPA—isopropyl alcohol.
Gantrez® AN119—a methyl vinyl ether-maleic anhydride copolymer having a molecular weight of 20,000 grams per gram mole, available from ISP Technology, Wayne, N.J.
MEK—methyl ethyl ketone.
PVP—polyN-vinylpyrrolidone having a K-valve of K-90.
CMC—Carboxymethyl cellulose having a molecular weight of about 250,000 grams per gram mole available as 99-7M8SXF from Aqualon Company, Willmington, Del.
DAA—Diacetone alcohol.
PVC drain tubes—20 French size
Carboxyl Vinyl Resin-I—a vinyl-chloride-vinyl acetate maleic acid (81-17-2 weight %) copolymer having a molecular weight of 15,000 grams per gram mole.
Carboxyl Vinyl Chloride Resin-II—a vinyl-chloride-vinyl acetate-maleic acid (83-16-1 weight %) copolymer having a molecular weight of 19,000 grams per gram mole.
Carboxyl Vinyl Chloride Resin-III—a vinyl chloride-vinyl acetate-hydroxyalkyl acrylate-carboxyl-containing copolymer, having a molecular weight of 26,000 grams per gram mole available as Bakelite Waterborne Solution Vinyl AW875 from Union Carbide Corporation, Danbury, Conn.
Tygon® tubing—0.25 inch ID, 0.375 inch OD.
Cationic HEC1—a quaternized hydroxyethyl cellulose having a molar and degree of substitution of 2.3 and 1.85, respectively, and a molecular weight of 750,000 grams per gram mole.
Cationic HEC2—a quaternized hydroxyethyl cellulose having a molar and degree of substitution of 2.3 and 1.85, respectively, and a molecular weight of 300,000 grams per gram mole
PET—polyethylene terephthalate balloon catheters.
Polyethylene balloons—2.5 cm dilatation balloons.
PET balloons—6.5 cm dilatation balloons.
Butyl glycol ether—ethylene glycol monobutyl ether.

In the Examples, two substrates were used for each test because the Coefficient of Friction Test requires two substrates to be run in parallel. One of the substrates was used for the Contact Angle Test, and an average of three readings is reported.

Example C-1

One pair of PVC Tygon tubes were wiped with a tissue containing IPA and air dried for 10 minutes ("min."). The clean tubes were dipped in an 1% solution of Gantrez® AN119 in MEK for 10 seconds ("sec.") and followed by drying in a forced air oven at 90° C. for 30 minutes. The tubes were then dipped into a 2 wt % solution of PVP in an IPA/water (70/30 wt %) mixture for 1 minute and followed by drying in a forced-air oven at 90° C. for 1 hour. The coated tube had a water contact angle of 16°. The coated tube was lubricious initially, but the lubricity was lost immediately upon touching showing a lack of durability. This Example demonstrates that despite the presence of the vinyl moiety, the lack of the carboxylic acid moiety in the binder polymer provided a coating with inferior abrasion resistance.

Example 2

Example 1 was repeated with the exception that after the PVC Tygon tubes were coated with the first coating solution and dried at 90° C. for 30 min they were soaked in distilled water overnight before the second coating was applied in order to promote the hydrolysis of the anhydride groups to carboxylic acid groups. The coated tubes were lubricious initially and gradually lost their lubricity after 100 abrasions as evidenced by the following data:

| Sample | Contact Angle | Coefficient of Friction | |
|---|---|---|---|
| | | Before Abrasion | After Abrasion |
| 2 | 32° | 0.12 | 0.45 |
| Uncoated | 77° | 0.5 | 0.5 |

Quite surprisingly, the coating of this Example 2 appeared to be more durable than that in the Example 1 since there was only a gradual reduction in lubricity. Moreover, the coated tube showed no apparent lubricity reduction during the early stage of Abrasion Test. Thus, the data from this Example 2 demonstrate, quite surprisingly, that the presence of carboxylic acid groups, which were present as a result of hydrolysis of the anhydride groups in the binder polymer, enhanced the abrasion resistance of the coating as compared to the coating of Example 1, which contained a vinyl moiety, but no carboxylic acid moiety.

Example C-3

Two pieces of PVC endotracheal tubes were wiped with a tissue containing IPA, air dried, and subsequently dipped in a 2 wt % PVP solution in diacetone alcohol for 5 min. The tubes were dried in a forced air oven at 90° C. for 2.5 hours. The finished coating was lubricious but slimy. Lubricity was lost rapidly upon touching, and essentially all coating was removed from the tubes after abrasion.

| Sample | Contact Angle | Coefficient of Friction | |
|---|---|---|---|
| | | Before Abrasion | After Abrasion |
| C-3 | 14° | 0.05 | 0.21 |
| Uncoated | 80° | 0.25 | 0.25 |

Example C-4

Example C-3 was repeated with the exception that a coating solution containing 0.2 wt % of vinyl chloride resin I in diacetone alcohol was used. The finished coating showed a moderate increase in hydrophilicity but was not lubricious in water. The Abrasion Resistance Test was not conducted.

| Sample | Contact Angle | Coefficient of Friction Before Abrasion |
|---|---|---|
| C-4 | 58° | 0.25 |
| Uncoated | 80° | 0.25 |

Examples C-3 and C-4 illustrate that neither a hydrophilic polymer nor a vinyl polymer alone is sufficient to provide an adherent lubricious coating.

Example 5

Two pieces of PVC drain tubes were cleaned with IPA and air dried. The cleaned tubes were dipped in an 1 wt % solution of carboxyl vinyl chloride resin-I in ethyl acetate for 30 sec. and followed by drying in a forced air oven at 90° C. for 30 min. The dried tubes were then dipped in a 1 wt % solution of PVP in a water/IPA mixture (57/43 wt. %) for 30 sec. and followed by drying in a forced air oven at 90° C. for 1 hour ("hr"). The finished coating was uniform, optically clear in both the dry or hydrated state, and very lubricious upon exposure to water. The contact angles with water were measured to be 66° and 10° for the uncoated and coated tubes showing a high degree of hydrophilicity of the coated surfaces. The coefficient of friction measured in the presence of water for the uncoated and coated tubes was 0.32 and 0.15, respectively, showing a significant reduction in friction. The wet tubes were subsequently abraded against an elastomer grommet for 100 times and the coefficient of friction remeasured. The value was 0.21 which was still substantially lower than that of the uncoated tubes.

Example 6

Example 5 was repeated with the exception that a 2 wt % PVP solution instead of 1 wt % solution was used. The finished coating was uniform, optically clear, and lubricious upon hydration. The contact angle measured in water was 13°. The coefficient of friction before and after 100 abrasions were found to be 0.15 and 0.19, respectively.

Example 7

Example 5 was repeated with the exception that an 0.5 wt % solution of carboxyl vinyl chloride resin-II in ethyl acetate and a 2.5 wt % solution of PVP in a mixture of IPA/diacetone alcohol (50/50 wt %) were used. The finished coating was uniform, optically clear, and lubricious upon hydration. The contact angle measured with water was 35°, and the coefficient of friction measured before and after 100 abrasions was 0.03 and 0.09, respectively.

Example 8

Sections of Tygon tubing were cleaned with IPA and air dried. The tubing sections were dipped in a 1 wt % carboxyl vinyl chloride resin-I solution in ethyl acetate for 30 sec. and followed by drying in a forced air oven at 90° C. for 30 min. The tubing sections were then dipped into an 0.5 wt % cationic HEC solution (50/50 wt % blend of cationic HEC1 and cationic HEC2) in a solvent mixture consisting of 95/5 weight % of water/IPA for 30 sec. and followed by drying at 90° C. for one hour. The finished coating was uniform, optically clear in both the dry and wet state, and very lubricious upon hydration. Contact angles with water for the uncoated and coated tubing were 76° and 10°, respectively, showing a high degree of hydrophilicity of the coated surfaces. The coefficient of friction before and after 100 abrasions for the uncoated and coated tubing were found to be 0.68/0.68 and 0.1/0.03, respectively.

Example 9

Twelve inch sections of a polyethylene catheter were cleaned with IPA and air dried. The catheters were dipped into a 1 wt % solution of carboxyl vinyl chloride resin-I in ethyl acetate for 30 sec. and followed by drying in a forced air oven at 65° C. for one hour. The catheters were subsequently dipped in a 0.5 wt % cationic HEC (same composition as used in Example 8) solution for 30 sec. and followed by drying in a forced air oven at 65° C. for 2 hrs. The coating was uniform and smooth. The coefficient of friction for the uncoated and coated catheters were measured to be 0.86 and 0.27, respectively.

Example 10

Polyethylene balloons were cleaned with IPA and air dried. The balloons were than coated with a 1 wt % solution of carboxyl vinyl chloride resin-I in ethyl acetate, by dipping for 30 sec. The balloons were allowed to dry in a forced air oven at 65° C. for 1 hour, and were subsequently dipped in a 0.5 wt. % cationic HEC solution (same composition as used in Example 8) for 30 sec. A 2-hour forced-air oven dry at 65° C. followed. The coatings obtained were smooth and very lubricious when wet. A coated balloon was dipped into a solution containing 500 units per ml of heparin for 1 minute and air dried. The presence of immobilized heparin in the coating was confirmed by infrared spectroscopy.

Example 11

PET balloons were cleaned with IPA and air dried. The balloons were than coated with a 1 wt % solution of carboxy vinyl chloride resin-I in ethyl acetate, by dipping 1 min. The balloons were allowed to dry in a forced air oven at 75° C., for 30 min. and were subsequently dipped in a 0.5 wt % cationic HEC solution (same composition as used in Example 8) for 1 sec. A 1-hour forced-air oven dry at 75° C. followed. The coatings obtained were smooth and very lubricious when wet. A coated balloon was dipped into a solution containing 500 units per ml of heparin for 1 minute and air dried. The presence of immobilized heparin in the coating was confirmed by infrared spectroscopy.

Examples 12-13

A 1 wt % solution of carboxyl vinyl chloride resin-I solution in diacetone alcohol was prepared by mixing in a Waring blender for about 10 min. to give a clear solution having a Brookfield viscosity of 8 centipoises ("cP"). A 2.5 wt % solution of PVP in diacetone alcohol was prepared in the same manner to give a clear solution having a Brookfield viscosity of 36 cP. The two solutions were combined in the weight ratios of 2/1 and 4/1 to yield solutions containing different ratios of the two polymers:

| Solution | PVP/Resin-I ratio | Total Solids % | Brookfield Vis., cP |
|---|---|---|---|
| A | 2/1 | 2.0 | 25 |
| B | 4/1 | 2.2 | 30 |

Four pieces of PVC endotracheal tubes were cleaned with IPA and air dried. Two tubes were dipped in Solution A for 30 sec. and followed by drying in a forced air oven at 90°

C. for 2.5 hrs. The other two tubes were dipped in Solution B for 30 sec. and followed by drying at 90° C. for 2.5 hrs. The finished tubes were uniform, optically clear in both the dry and wet state, and very lubricious upon hydration. Surface characterizations gave the following results:

| Solution Used | Contact Angle with Water | Coefficient of Friction | Coefficient of Friction After Abrasion (100 times) |
|---|---|---|---|
| Uncoated | 80 | 0.25 | 0.25 |
| A | 30 | 0.14 | 0.17 |
| B | 22 | 0.09 | 0.11 |

Examples 14–18

One-step coating solutions of carboxyl vinyl chloride resin-I and PVP, at 2.2% total solids, in diacetone alcohol were prepared on a roll mill at varying polymer ratios as shown below:

| Solution | PVP/Resin-I | Total Solids % | Brookfield Viscosity, cP. |
|---|---|---|---|
| 1 | 4/1 | 2.2 | 30 |
| 2 | 5/1 | 2.2 | 29 |
| 3 | 7/1 | 2.2 | 32 |
| 4 | 10/1 | 2.2 | 34 |

PVC endotracheal tubes were coated with the above solutions according to the following procedure. The tubes were wiped with IPA and allowed to air dry for 10 min. A pair of the tubes was then dipped into each of the above solutions for a specified time (indicated below) and subsequently dried in a forced air oven at 90° C. for 2.5 hours. The lubricity, before and after 100 abrasions with a silicone elastomer grommet, of the coated tubes was characterized by measuring the coefficient of friction in the presence of water. In addition, the contact angle was also measured and showed a high degree of hydrophilicity for the coated tubes.

| | | | Coefficient of Friction | | |
|---|---|---|---|---|---|
| Example | Solution | Dipping Time, min. | Before Abrasion | After Abrasion | Contact Angle, ° |
| 14 | 1 | 5 | 0.07 | 0.08 | 22 |
| 15 | 2 | 0.5 | 0.09 | 0.14 | 22 |
| 16 | 3 | 2.45 | 0.09 | 0.08 | 22 |
| 17 | 4 | 0.5 | 0.09 | 0.07 | 23 |
| 18 | 4 | 5 | 0.09 | 0.08 | 25 |
| Uncoated Tube | | | 0.25 | 0.25 | 81 |

Example 19

A water-borne one-step coating fluid of carboxyl vinyl chloride resin-III and PVP, at 2.2% total solids, was prepared in an aqueous medium containing 80% diacetone alcohol and 20% water. The ratio between PVP and the vinyl resin was 10:1. The dispersion was uniform and slightly hazy and showed a Brookfield viscosity of 45 cP. Two pieces of PVC endotracheal tubes were coated according to the some procedure described in Examples 14 with a 5 min. dip in the coating solution and followed by a 1.5 hours drying at 90° C. The coating was clear and uniform, and was characterized using the same methods described in Examples 14.

| Sample | Contact Angle, ° | Coefficient of Friction | |
|---|---|---|---|
| | | Before Abrasion | After Abrasion |
| Uncoated | 80 | 0.25 | 0.25 |
| 8 | 23 | 0.05 | 0.06 |

Example 20

A water-borne coating formulation was prepared by mixing carboxyl vinyl chloride resin-III and PVP in butyl glycol ether, diacetone alcohol, and water mixture to give the following composition:

| | wt % |
|---|---|
| Carboxyl vinyl chloride resin-III | 0.4% |
| PVP | 4% |
| Butyl Glycol Ether | 20% |
| Diacetone Alcohol | 20% |
| Water | 55.6% |
| Brookfield Viscosity, cP | 89 |

Two pieces of PVC endotracheal tubes were dipped in the above solution for 5 minutes and dried in a forced air oven at 90° C. for 1.5 hours. The finished coating was uniform. The contact angle with water was 44.7°, and coefficient of friction in the presence of water was measured to be 0.03 and 0.07 after 100 abrasions with an elastic membrane. The uncoated PVC endotracheal tube showed corresponding values of 80°, 0.25, and 0.25, respectively.

Example 21

Two pieces of Tygon tubes were coated according to Example 14 with the exception that the carboxyl vinyl resin-I was replaced with a low molecular weight vinyl acetate-acrylic acid copolymer (99.2 wt % vinyl acetate/0.8 wt % acrylic acid). The coated tubes were lubricious and showed COF before and after 100 abrasions of 0.25 and 0.36, respectively. The uncoated tube showed a COF of 0.51. The contact angle with distilled water for the coated and uncoated tubes were 10° and 77°, respectively.

Although the invention has been described above with respect to specific aspects, those skilled in the art will recognize that other aspects are intended to be included within the scope of the claims which follow. For instance, polymers other than the specific binder polymers and hydrophilic polymers may be employed in accordance with the present invention. In addition, other carboxylic acids such as, for example, halide-substituted carboxylic acids such as chlorocetic acids or amino acids may be utilized instead of the specific carboxylic acids disclosed. Moreover, in addition to the specific vinyl moieties set forth above, other vinyl moieties such as, for examples, those found in compounds such as vinyl benzene, vinyl toluene, methyl methacrylate and acrylonitrile may be used in accordance with the present invention.

We claim:

1. In a lubricious coating applied to a surface of a substrate comprising:
   (i) a hydrophilic polymer which is substantially more lubricious when wetted with an aqueous liquid than when dry; and
   (ii) a binder polymer comprising a vinyl moiety which is capable of bonding to the surface of the substrate and the hydrophilic polymer;

the improvement wherein (i) the binder polymer is a copolymer comprising the polymeric reaction product of vinyl chloride, vinyl acetate and a carboxylic acid and (ii) there is a substantial absence of covalent bonding between the binder polymer and the hydrophilic polymer.

2. The lubricious coating of claim 1 wherein the carboxylic acid comprises from 1 to about 26 carbon atoms per molecule.

3. The lubricious coating of claim 1 wherein said substrate is selected from the group consisting of polyurethane, polyvinyl chloride, polyacrylate, polycarbonate, polystryrene, polyester resins, polybutadiene-styrene copolymers, nylon, polyethylene, polypropylene, polybutylene, silicon, polyvinyl acetate, polymethacrylate, polysulfone, polyisoprene, copolymers and derivatives thereof, glass, metal, ceramic and mixtures thereof.

4. The lubricious coating of claim 1 wherein the binder polymer has a number average molecular weight of from about 5,000 to 1,000,000 grams per gram mole.

5. The lubricious coating of claim 1 wherein the hydrophilic polymer is selected from the group consisting of polyvinyl compounds, polysaccharides, polyurethanes, polyacrylates, polyacrylamides, polyalkyleneoxides and copolymers, complexes, derivatives and mixtures thereof.

6. The lubricious coating of claim 5 wherein the hydrophilic polymer is selected from the group consisting of polyN-vinylpyrrolidone, polyN-vinylpyrrolidone copolymers, carboxymethylcellulose, polyacrylic acid, cationically-modified hydroxyethylcellulose, polyethylene oxides, polyethylene oxide copolymers, and complexes, derivatives and mixtures thereof.

7. The lubricious coating of claim 5 wherein the hydrophilic polymer is cationic, anionic or amphoteric.

8. The lubricious coating of claim 7 which further comprises an additive which is ionically bonded or hydrogen bonded to the hydrophilic polymer.

9. The lubricious coating of claim 8 wherein the additive is selected from the group consisting of therapeutic agents, antithrombogenic agents, antimicrobial agents, antibiotics and mixtures thereof.

10. The lubricious coating of claim 1 which comprises an inner layer of binder polymer which contacts the surface of the substrate and an outer layer of hydrophilic polymer which contacts the inner layer.

11. The lubricious coating of claim 10 which further comprises a colorant or antimicrobial in one or both of the inner layer or the outer layer.

12. The lubricious coating of claim 1 which comprises a single layer containing a substantially homogeneous mixture of the binder polymer and the hydrophilic polymer.

13. A biomedical device comprising the lubricious coating of claim 1.

14. The biomedical device of claim 13 which is selected from the group consisting of catheters, guide wires, stents, dilatation balloons, endotracheal tubes, instruments, and implants.

15. In a lubricious coating applied to a surface of a substrate comprising:
 (i) a hydrophilic polymer which is substantially more lubricious when wetted with an aqueous liquid than when dry; and
 (ii) a binder polymer which is capable of bonding to the surface of the substrate and the hydrophilic polymer;
 the improvement wherein: (a) the binder polymer is a copolymer of vinyl chloride, vinyl acetate and at least one of maleic acid or acrylic acid; (b) there is a substantial absence of covalent bonding between the binder polymer and the hydrophilic polymer; and (c) the hydrophilic polymer is poly N-vinylpyrrolidone.

16. A lubricious coating applied to a surface of a substrate comprising:
 (i) an outer layer comprising greater than 50% of a hydrophilic polymer which is substantially more lubricious when wetted with an aqueous liquid than when dry; and
 (ii) an inner layer comprising greater than 50% of a binder polymer contacting the surface of the substrate and the outer layer;
wherein: (i) the binder polymer is a copolymer comprising the polymeric reaction product of vinyl chloride, vinyl acetate and a carboxylic acid; and (ii) there is a substantial absence of covalent bonding between the binder polymer and the hydrophilic polymer.

17. The lubricious coating of claim 16 wherein the binder polymer is a copolymer of vinyl chloride, vinyl acetate and at least one of maleic acid or acrylic acid.

* * * * *